United States Patent
Ameri (10) Patent No.: US 8,311,637 B2
(45) Date of Patent: Nov. 13, 2012

(54) MAGNETIC CORE FLUX CANCELING OF FERRITES IN MRI

(75) Inventor: Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 748 days.

(21) Appl. No.: 12/367,452

(22) Filed: Feb. 6, 2009

(65) Prior Publication Data

US 2009/0204182 A1    Aug. 13, 2009

Related U.S. Application Data (60) Provisional application No. 61/027,751, filed on Feb. 11, 2008.

(51) Int. Cl.
*A61N 1/08* (2006.01)
*A61N 1/378* (2006.01)

(52) U.S. Cl. ............. 607/61; 607/60; 607/30; 607/31; 607/32; 607/33

(58) Field of Classification Search ............... 607/63, 607/30–33, 60–61
See application file for complete search history.

(56) References Cited

U.S. PATENT DOCUMENTS

| | | |
|---|---|---|
| 3,888,260 A | 6/1975 | Fischell |
| 3,898,995 A | 8/1975 | Dresbach |
| 4,091,818 A | 5/1978 | Brownlee et al. |
| 4,379,459 A | 4/1983 | Stein |
| 4,404,125 A | 9/1983 | Abolins et al. |
| 4,516,579 A | 5/1985 | Irnich |
| 4,611,127 A | 9/1986 | Ibrahim et al. |
| 4,694,837 A | 9/1987 | Blakeley et al. |
| 4,729,376 A | 3/1988 | DeCote, Jr. |
| 4,751,110 A | 6/1988 | Gulla et al. |
| 4,779,617 A | 10/1988 | Whigham |
| 4,823,075 A * | 4/1989 | Alley ................. 324/117 H |
| 4,869,970 A | 9/1989 | Gulla et al. |

(Continued)

FOREIGN PATENT DOCUMENTS

EP    0530006    3/1993

(Continued)

OTHER PUBLICATIONS

Kerr, Martha, Shock Rate Cut 70% With ICDs Programmed to First Deliver Antitachycardia Pacing: Results of the PainFREE Rx II Trial, Medscape CRM News, May 21, 2003.

(Continued)

*Primary Examiner* — Joseph Stoklosa
(74) *Attorney, Agent, or Firm* — Faegre Baker Daniels LLP (57) ABSTRACT

A magnetic core flux canceling device according to embodiments of the present invention includes a magnetic field sensor adapted for placement at a ferrite material core in an implantable medical device, the magnetic field sensor adapted to transmit a signal corresponding to a magnitude of a first magnetic field. Such a device may also include a coil disposed around the ferrite material core and a driver circuit configured to receive the signal and to vary a voltage applied across the coil based on the signal, the voltage applied across the coil creating a second magnetic field at least partially in a direction opposite the first magnetic field. According to some embodiments of the present invention, multiple coils may be used to cancel magnetic fields in multiple directions. A voltage applied across the coil varies in magnitude and/or direction to cancel or weaken an MRI-related magnetic field.

21 Claims, 4 Drawing Sheets

U.S. PATENT DOCUMENTS

| | | | |
|---|---|---|---|
| 4,934,366 A | 6/1990 | Truex et al. |
| 5,038,785 A | 8/1991 | Blakeley et al. |
| 5,075,039 A | 12/1991 | Goldberg |
| 5,076,841 A | 12/1991 | Chen et al. |
| 5,120,578 A | 6/1992 | Chen et al. |
| 5,187,136 A | 2/1993 | Klobucar et al. |
| 5,188,117 A | 2/1993 | Steinhaus et al. |
| 5,197,468 A | 3/1993 | Proctor et al. |
| 5,217,010 A | 6/1993 | Tsilik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,990 A | 8/1995 | Wahlstrand et al. |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,683,434 A | 11/1997 | Archer |
| 5,687,735 A | 11/1997 | Forbes et al. |
| 5,694,952 A | 12/1997 | Lidman et al. |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | Smith et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spher |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,607,485 B2 | 8/2003 | Bardy |
| 6,626,937 B1 | 9/2003 | Cox |
| 6,629,938 B1 | 10/2003 | Engvall |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 * | 5/2005 | Hrdlicka et al. ............... 607/27 |
| 6,925,328 B2 | 8/2005 | Foster et al. |
| 6,937,906 B2 | 8/2005 | Terry et al. |
| 6,944,489 B2 | 9/2005 | Zeijlemaker et al. |
| 6,963,779 B1 | 11/2005 | Shankar |
| 7,013,180 B2 | 3/2006 | Villaseca et al. |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 | 1/2007 | Kroll et al. |
| 7,174,219 B2 | 2/2007 | Wahlstrand et al. |

| | | |
|---|---|---|
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |
| 7,272,444 B2 | 9/2007 | Peterson et al. |
| 7,369,898 B1 | 5/2008 | Kroll et al. |
| 7,388,378 B2 | 6/2008 | Gray et al. |
| 7,509,167 B2 | 3/2009 | Stessman |
| 7,561,915 B1 | 7/2009 | Cooke et al. |
| 7,835,803 B1 | 11/2010 | Malinowski et al. |
| 7,839,146 B2 * | 11/2010 | Gray .............................. 324/318 |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0082648 A1 | 6/2002 | Kramer et al. |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton, Jr. et al. |
| 2002/0166618 A1 | 11/2002 | Wolf et al. |
| 2002/0175782 A1 | 11/2002 | Trihn et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton, Jr. et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1 | 10/2003 | Greatbatch |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0049237 A1 | 3/2004 | Larson et al. |
| 2004/0088012 A1 | 5/2004 | Kroll et al. |
| 2004/0093432 A1 | 5/2004 | Luo et al. |
| 2004/0263174 A1 * | 12/2004 | Gray et al. .................... 324/322 |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0197677 A1 * | 9/2005 | Stevenson ....................... 607/36 |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0167496 A1 | 7/2006 | Nelson et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |
| 2007/0255332 A1 | 11/2007 | Cabelka et al. |
| 2008/0033497 A1 | 2/2008 | Bulkes et al. |
| 2008/0132985 A1 | 6/2008 | Wedan et al. |
| 2008/0221638 A1 | 9/2008 | Wedan et al. |
| 2009/0138058 A1 | 5/2009 | Cooke et al. |
| 2009/0149906 A1 | 6/2009 | Ameri et al. |
| 2009/0149909 A1 | 6/2009 | Ameri |
| 2009/0210025 A1 | 8/2009 | Ameri |
| 2010/0087892 A1 | 4/2010 | Stubbs et al. |
| 2010/0211123 A1 | 8/2010 | Stubbs et al. |
| 2011/0270338 A1 | 11/2011 | Cooke et al. |
| 2011/0276104 A1 | 11/2011 | Ameri et al. |
| 2012/0071941 A1 | 3/2012 | Ameri |

FOREIGN PATENT DOCUMENTS

| | | |
|---|---|---|
| EP | 0591334 | 4/1994 |
| EP | 0705621 | 4/1996 |
| EP | 0719570 | 7/1996 |
| EP | 0836413 | 4/1998 |
| EP | 0331959 | 9/1998 |
| EP | 0870517 | 10/1998 |
| EP | 0891207 | 1/1999 |
| EP | 0891786 | 1/1999 |
| EP | 0980105 | 2/2000 |
| EP | 0989623 | 3/2000 |

| | | |
|---|---|---|
| EP | 0989624 | 3/2000 |
| EP | 1007132 | 6/2000 |
| EP | 1007140 | 6/2000 |
| EP | 1060762 | 12/2000 |
| EP | 1061849 | 12/2000 |
| EP | 1109180 | 6/2001 |
| EP | 1128764 | 9/2001 |
| EP | 1191556 | 3/2002 |
| EP | 1271579 | 1/2003 |
| EP | 1308971 | 5/2003 |
| EP | 1372782 | 1/2004 |
| WO | WO 91/04069 | 4/1991 |
| WO | WO 96/38200 | 12/1996 |
| WO | WO 97/12645 | 4/1997 |
| WO | WO 00/54953 | 9/2000 |
| WO | WO 01/37286 | 5/2001 |
| WO | WO 01/80940 | 11/2001 |
| WO | WO 01/86774 | 11/2001 |
| WO | WO 02/056761 | 7/2002 |
| WO | WO 02/065895 | 8/2002 |
| WO | WO 02/072004 | 9/2002 |
| WO | WO 02/089665 | 11/2002 |
| WO | WO 02/092161 | 11/2002 |
| WO | WO 03/013199 | 2/2003 |
| WO | WO 03/037399 | 5/2003 |
| WO | WO 03/059445 | 7/2003 |
| WO | WO 03/061755 | 7/2003 |
| WO | WO 03/063946 | 8/2003 |
| WO | WO 03/063952 | 8/2003 |
| WO | WO 03/063954 | 8/2003 |
| WO | WO 03/063955 | 8/2003 |
| WO | WO 03/063956 | 8/2003 |
| WO | WO 03/063958 | 8/2003 |
| WO | WO 03/063962 | 8/2003 |
| WO | WO 03/070098 | 8/2003 |
| WO | WO 03/073449 | 9/2003 |
| WO | WO 03/073450 | 9/2003 |
| WO | WO 03/086538 | 10/2003 |
| WO | WO 03/090846 | 11/2003 |
| WO | WO 03/090854 | 11/2003 |
| WO | WO 03/095022 | 11/2003 |
| WO | WO 2006/124481 | 11/2006 |

OTHER PUBLICATIONS

Schueler et al., "MRI Compatibility and Visibility Assessment of Implantable Medical Devices", Journal of Magnetic Resonance Imaging, 9:596-603 (1999).

Sweeney, Michael O. et al., Appropriate and Inappropriate Ventricular Therapies, Quality of Life, and Mortality Among Primary and Secondary Prevention Implantable Cardioverter Defibrillator Patients: Results From the Pacing Fast VT REduces Shock ThErapies (PainFREE Rx II) Trial, American Heart Association, 2005.

Wilkoff, Bruce L. et al., "A Comparison of Empiric to Physician-Tailored Programming of Implantable Cardioverter-Defibrillators Results From the Prospective Randomized Multicenter EMPIRIC Trial," Journal of the American College of Cardiology, vol. 48, No. 2, 2006. doi:10.1016/j.jacc.2006.03.037.

File History for U.S. Appl. No. 11/015,807, filed Dec. 17, 2004.

Dempsey Mary F. et al., "Investigation of the Factors Responsible for Burns During MRI", *Journal of Magnetic Resonance Imaging* 2001;13:627-631.

Luechinger, Roger et al., "In vivo heating of pacemaker leads during magnetic resonance imaging", *European Heart Journal* 2005;26:376-383.

Shellock, Frank G. et al., "Cardiovascular catheters and accessories: ex vivo testing of ferromagnetism, heating, and artifacts associated with MRI", *Journal of Magnetic Resonance Imaging*, Nov./Dec. 1998; 8:1338-1342.

Shellock FG, "Reference manual for magnetic resonance safety, implants, and devices", pp. 136-139, 2008 ed. Los Angeles; Biomedical Research Publishing Group; 2008.

International Search Report and Written Opinion issued in PCT/US2009/068314, mailed Mar. 25, 2009, 14 pages.

* cited by examiner

MAGNETIC CORE FLUX CANCELING OF FERRITES IN MRI

CROSS-REFERENCE TO RELATED APPLICATIONS

This application claims the benefit of U.S. Provisional Patent Application Ser. No. 61/027,751, filed on Feb. 11, 2008, and entitled, "MAGNETIC CORE FLUX CANCELING OF FERRITES IN MRI," which is incorporated by reference herein in its entirety for all purposes.

TECHNICAL FIELD

Embodiments of the present invention relate to medical devices and the simultaneous delivery of diagnostic and therapeutic treatments. More specifically, embodiments of the present invention relate to devices and methods for delivery of cardiovascular diagnostic or pacing therapy in a magnetic field environment.

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, a static magnetic field produced by the MRI system can saturate ferrite materials used in circuits such as inductors and transformers within implantable medical devices such as pacemakers or cardiac defibrillators. Saturation of the ferrite components can disrupt the functionality of such devices. Accordingly, there is an ongoing need for devices and methods for shielding medical devices from magnetic fields during medical procedures such as magnetic resonance imaging (MRI).

SUMMARY

According to embodiments of the present invention, a magnetic field sensor is placed near a ferrite material core in an implantable medical device. The magnetic sensor sends a signal corresponding to a magnitude of a magnetic field near the ferrite material core, and a low pass filter operates on the signal to remove signal components associated with normal operation of the ferrite material core. A coil is disposed around the ferrite material core, and a driver circuit receives the filtered signal and varies a voltage applied across the coil to create a magnetic field in a direction opposite that of the sensed magnetic field, according to embodiments of the present invention. A magnetic field produced in the coil may thus be used to cancel a magnetic field produced by an MRI system, to thereby substantially prevent saturation of the ferrite material core by the magnetic field of the MRI.

While some embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the appended claims.

DETAILED DESCRIPTION

Figure 1:
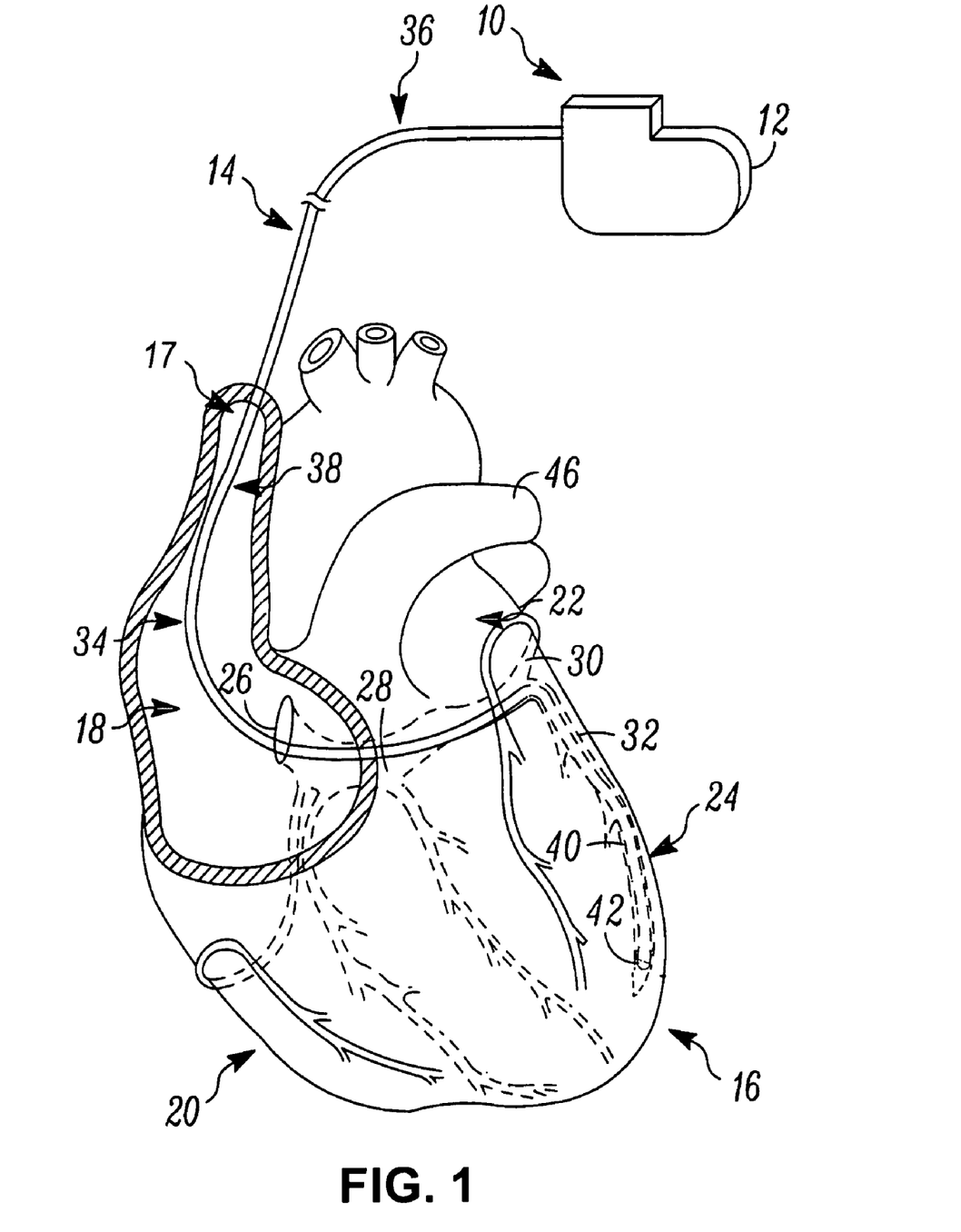
FIG. 1 is a schematic drawing of a cardiac rhythm management system including a pulse generator coupled to a lead deployed in a patient's heart, according to embodiments of the present invention.

FIG. 1 is a schematic drawing of a cardiac rhythm management system 10 including a pulse generator 12 coupled to a lead 14 deployed in a patient's heart 16 from a superior vena cava 17. As is known in the art, the pulse generator 12 is typically implanted subcutaneously at an implantation location in the patient's chest or abdomen. As shown, the heart 16 includes a right atrium 18 and a right ventricle 20, a left atrium 22 and a left ventricle 24, a coronary sinus ostium 26 in the right atrium 18, a coronary sinus 28, and various cardiac branch vessels including a great cardiac vein 30 and an exemplary branch vessel 32.

As shown in FIG. 1, the lead 14 may include an elongate body 34 including a proximal region 36 and a distal region 38. The distal region 38 has a distal end 40 including an electrode 42, according to embodiments of the present invention. The lead 14 includes a lead conductor which conductively connects the pulse generator 12 to the electrode 42, according to embodiments of the present invention. To facilitate left ventricular pacing epicardially via a transvenous approach, leads 14 may be deployed in coronary veins 32 through the coronary sinus 28. Although FIG. 1 depicts the lead 14 as part of a cardiac rhythm management system 10 with an electrode 42, the lead 14 may alternatively include one or more sensors and/or one or more electrodes 42, and may couple the one or more sensors with a monitor instead of and/or in addition to the pulse generator 12.

Figure 2:
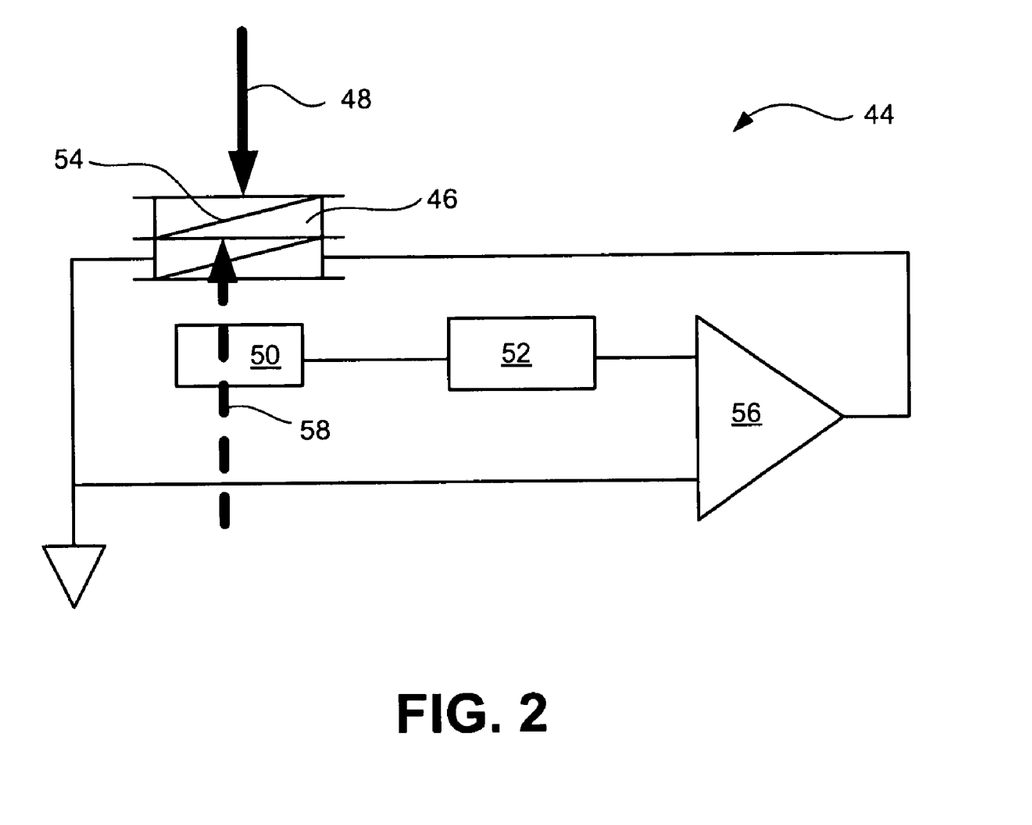
FIG. 2 is a schematic diagram of a magnetic field cancellation circuit, according to embodiments of the present invention.

FIG. 2 is a schematic diagram of a magnetic field cancellation circuit 44, according to embodiments of the present invention. A ferrite material core 46 is typically found within inductors and transformers, and such components can be found within implantable medical devices such as pacemakers or cardiac defibrillators. During an MRI procedure, a static magnetic field 48 produced by the MRI system can saturate the ferrite materials 46, disrupting the functionality of such devices.

According to embodiments of the present invention, a magnetic sensor 50 may be placed within, at, and/or near the ferrite material core 46. The magnetic sensor 50 may be a Hall effect sensor, for example. The magnetic sensor 50 outputs a voltage signal which varies according to the magnitude of the static magnetic field 48, according to embodiments of the present invention. Due to its proximity to the ferrite material core 46, the magnetic sensor 50 may also sense changes in magnetic field resulting from a normal operation of the ferrite material core 46. For example, the ferrite material core 46 may be an inductor or transformer, which uses a generated magnetic field during normal operation. A filter 52, such as a low pass filter, may be electrically coupled to the magnetic sensor 50 in order to remove the higher frequency components of the output of the magnetic sensor 50, which are typically associated with normal operation of the ferrite material core 46, according to embodiments of the present invention.

A coil or winding of wire 54 may be wound around the ferrite material core 46, according to embodiments of the present invention. According to other embodiments of the present invention, the coil 54 is not wound directly around the ferrite material core 46, but is placed in sufficient proximity to (e.g. above, below, to the side of) the ferrite material core 46 such that a current passed through the coil 54 creates a magnetic field at the ferrite material core 46. A driver circuit 56 is configured to vary the voltage applied across the coil 54 in order to drive current into the coil 54 to produce a magnetic field 58 opposing the magnetic field 48 generated by the MRI system, according to embodiments of the present invention. The driver circuit 56 may be, for example, a comparator or a high gain differential circuit, according to embodiments of the present invention.

According to some embodiments of the present invention, because the magnetic sensor 50 provides an input to the driver circuit 56, the driver circuit 56 may increase the voltage applied across the coil 54 when the magnetic field 48 strength increases, and the driver circuit 56 may decrease or eliminate the voltage applied across the coil 54 when the magnetic field 48 decreases or goes to zero. In this way, the driver circuit 56 may dynamically vary the field strength of the magnetic field 58 to cancel or offset the magnetic field 48 of the MRI system, according to embodiments of the present invention. For example, even before a patient with an implantable medical device including a magnetic field cancellation circuit 44 is placed inside of the bore of an MRI device, the magnetic sensor 50 may sense the relatively weak static magnetic signal 48 outside of the MRI system and begin canceling it, according to embodiments of the present invention.

This behavior of the circuit 44 prevents the ferrite material core 46 from entering a saturation state, in which a large pulse of current, depending on the characteristics of the ferrite material core 46, is needed to bring the ferrite material core 46 out of saturation very fast. Because the magnetic field gradient around an MRI system is not a step function, but instead varies continuously based on distance, the magnetic sensor 50 can sense the presence of the static magnetic field 48 prior to being positioned inside the bore. This enables the circuit 44 to immediately begin canceling the magnetic field 48 when even a small static field 48 is detected, to prevent the core 46 from going into saturation reign, according to embodiments of the present invention. To minimize the induced current into the winding 54, the ferrite material core 46 should not be saturated. A large relative permeability of the unsaturated core 46, in addition to more wire turns in the coil 54, permit the coil 54 to produce magnetic fields 58 of the magnitude required to cancel the static magnetic field 48 of MRI systems, according to embodiments of the present invention.

In some embodiments of the present invention, the magnetic field 58 is equal in magnitude to the magnetic field 48 of the MRI, such that the sum of the static magnetic fields 48, 58 is zero. According to other embodiments of the present invention, the magnetic field 58 is smaller than the magnetic field 48, but large enough to prevent the ferrite material core 46 from rapidly reaching a saturation state.

Figure 3:
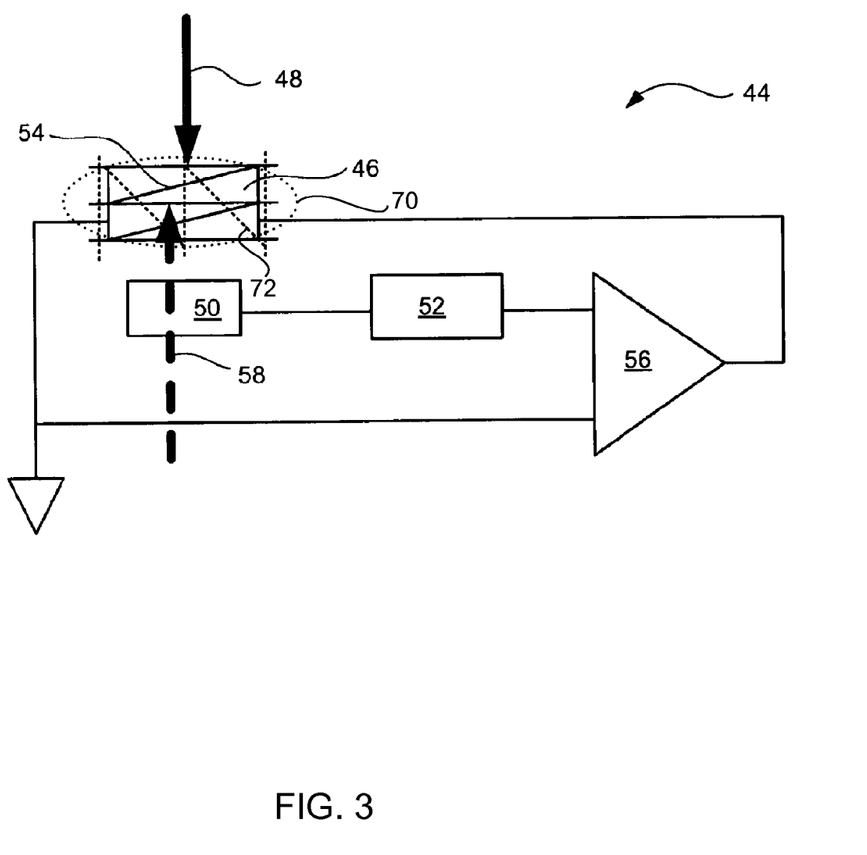
FIG. 3 is a schematic diagram of a magnetic field cancellation circuit, according to embodiments of the present invention.
Figure 4:
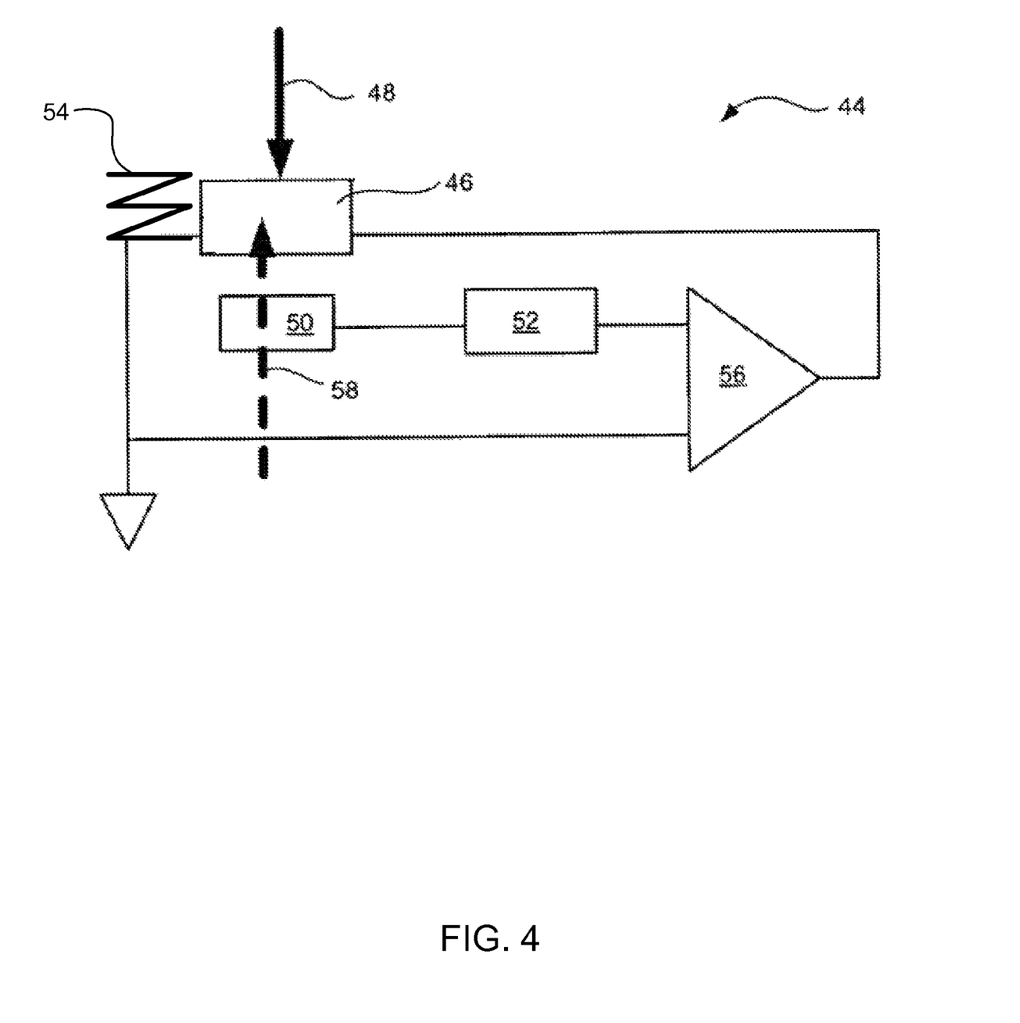
FIG. 4 is a schematic diagram of a magnetic field cancellation circuit, according to embodiments of the present invention.

According to some embodiments of the present invention, the cancellation circuit 44 may include circuitry to determine the direction of the MRI magnetic field 48 and to select the direction of the current applied through the coil 54 to create the magnetic field 58 in the direction opposing the MRI magnetic field 48. Embodiments of the present invention may include additional circuits 44 with coils 54 oriented in different directions (e.g. one for each of the x, y, and z axes, as shown in FIG. 3, in which the coil 54 is oriented along the y axis, coil 72 is oriented along the x axis, and coil 70 is oriented along the z axis) to cancel magnetic fields generated in other directions relative to the ferrite material core 46 or other ferrite material components. For example, embodiments of the present invention may include circuits 44 with coils 54 oriented to produce a magnetic field in each of the two directions orthogonal to the direction of magnetic field 58 as indicated in FIG. 2.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A device for use with a ferrite material core, the device comprising:
    a magnetic field sensor adapted for placement at the ferrite material core in an implantable medical device, the magnetic field sensor adapted to transmit a signal corresponding to a magnitude of a first static magnetic field at the ferrite material core;
    a coil configured to be disposed around the ferrite material core; and
    a driver circuit configured to receive the signal and to vary a voltage applied across the coil based on the signal, the voltage applied across the coil creating a second magnetic field at least partially in a direction opposite the first static magnetic field.

2. The device of claim 1, wherein the driver circuit is further configured to vary a polarity of the voltage applied across the coil to create the second magnetic field in one of two opposite directions.

3. The device of claim 1, wherein the coil is a first coil, the device further comprising:
    a second coil configured to be disposed around the ferrite material core, the second coil capable of generating a third magnetic field at least partially directed orthogonally to the second magnetic field.

4. The device of claim 3, further comprising:
    a third coil configured to be disposed around the ferrite material core, the third coil capable of creating a fourth magnetic field at least partially directed orthogonally to the first and second magnetic fields.

5. The device of claim 1, wherein the second magnetic field is equal in magnitude to the first magnetic field.

6. The device of claim 1, wherein the second magnetic field is smaller in magnitude than the first magnetic field, and wherein the second magnetic field is large enough to prevent the ferrite material core from entering a saturation state.

7. The device of claim 1, wherein the driver circuit is a comparator.

8. The device of claim 1, wherein the driver circuit is a high gain differential circuit.

9. The device of claim 1, wherein the device includes the ferrite core material and wherein the ferrite core material is a transformer core in the implantable medical device.

10. The device of claim 1, wherein the device includes the ferrite core material and wherein the ferrite core material is an inductor core in the implantable medical device.

11. The device of claim 1, wherein the magnetic field sensor is a Hall effect sensor.

12. The device of claim 1, wherein the first static magnetic field is an MRI field component.

13. A device for use with a ferrite material core, the device comprising:
  a magnetic field sensor adapted for placement near the ferrite material core in an implantable medical device, the magnetic field sensor adapted to measure a magnitude of a first magnetic field near the ferrite material core and to transmit a signal corresponding to the measured magnitude of the first magnetic field;
  a low pass filter adapted to filter the signal into a filtered signal;
  a coil configured to be disposed around the ferrite material core; and
  a driver circuit configured to receive the filtered signal and to vary a voltage applied across the coil based on the filtered signal, the voltage applied across the coil creating a second magnetic field at least partially in a direction opposite the first magnetic field.

14. The device of claim 13, wherein the driver circuit is a comparator.

15. The device of claim 13, wherein the driver circuit is a high gain differential circuit.

16. The device of claim 13, wherein the device includes the ferrite core material and wherein the ferrite core material is a transformer core in the implantable medical device.

17. The device of claim 13, wherein at least a portion of the first magnetic field results from normal operation of the ferrite material core, and wherein the low pass filter filters out components of the signal related to normal operation of the ferrite material core.

18. The device of claim 13, wherein the device includes the ferrite core material and wherein the ferrite core material is an inductor core in the implantable medical device.

19. The device of claim 13, wherein the magnetic field sensor is a Hall effect sensor.

20. The device of claim 13, wherein the magnetic field sensor is adapted to transmit a signal corresponding to a magnitude of a first static magnetic field near the ferrite material core.

21. A device comprising:
  a ferrite material core;
  a magnetic field sensor placed at the ferrite material core in an implantable medical device, the magnetic field sensor adapted to transmit a signal corresponding to a magnitude of a first magnetic field at the ferrite material core;
  a coil located to a side of the ferrite material core; and
  a driver circuit configured to receive the signal and to vary a voltage applied across the coil based on the signal, the voltage applied across the coil creating a second magnetic field at least partially in a direction opposite the first magnetic field.

* * * * *